United States Patent [19]

Matsumoto et al.

[11] Patent Number: 5,013,841
[45] Date of Patent: May 7, 1991

[54] OXO QUINOLINE DERIVATIVES

[75] Inventors: Jun-ichi Matsumoto, Ikoma; Akira Minamida, Takaishi; Masahiro Fujita, Kobe; Tohru Hirose, Kishiwada; Junji Nakano, Ikoma; Shinichi Nakamura, Takatsuki, all of Japan

[73] Assignee: Dainippon Pharmaceutical Co., Ltd., Osaka, Japan

[21] Appl. No.: 389,900

[22] Filed: Aug. 4, 1989

Related U.S. Application Data

[62] Division of Ser. No. 258,613, Oct. 17, 1988.

[30] Foreign Application Priority Data

Oct. 16, 1987 [JP] Japan ................. 62-262441
Apr. 30, 1988 [JP] Japan ................. 63-108840

[51] Int. Cl.$^5$ ............................................ C07D 401/00
[52] U.S. Cl. .................................................... 544/363
[58] Field of Search .......................................... 544/363

[56] References Cited

U.S. PATENT DOCUMENTS

| | | | |
|---|---|---|---|
| 4,668,680 | 5/1987 | Trehan et al. | 544/363 |
| 4,806,539 | 2/1989 | Petersen et al. | 544/363 |
| 4,886,810 | 12/1989 | Matsumoto et al. | 544/363 |
| 4,894,458 | 1/1990 | Masuzawa et al. | 544/363 |

FOREIGN PATENT DOCUMENTS

| | | |
|---|---|---|
| 0078362 | 5/1983 | European Pat. Off. . |
| 0113093 | 7/1984 | European Pat. Off. . |
| 0221463 | 5/1987 | European Pat. Off. . |
| 0284935 | 10/1988 | European Pat. Off. . |
| 0287951 | 10/1988 | European Pat. Off. . |
| 0312085 | 4/1989 | European Pat. Off. ............ 544/363 |

Primary Examiner—Frederick E. Waddell
Assistant Examiner—Raymond Covington
Attorney, Agent, or Firm—Wenderoth, Lind & Ponack

[57] ABSTRACT

A quinoline derivative of the formula

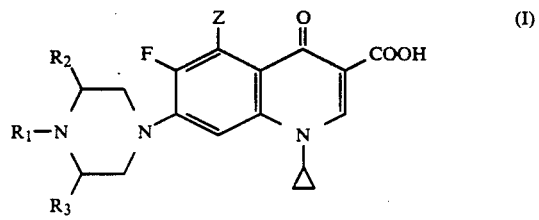

wherein Z is an amino group or a halogen atom, and $R_1$, $R_2$ and $R_3$ are the same or different and each represents a hydrogen atom or a lower alkyl group having 1 to 5 carbon atoms, and an ester thereof and a salt of the derivative or the ester and processes for preparation thereof. These compounds show excellent antibacterial activity and are useful as antibacterial agents.

4 Claims, No Drawings

OXO QUINOLINE DERIVATIVES

This application is a division of application Ser. No. 07/258,613, filed Oct. 17, 1988.

This invention relates to a novel quinoline derivative having very good antibacterial activity, processes for production thereof, and an antibacterial agent containing the quinoline derivative.

The prior art relating to pharmacologically effective compounds in this field will first be discussed briefly.

European Laid-Open Patent Specification No. 78,362 and its corresponding Japanese Laid-Open Patent Publication No. 74667/1983 disclose 1-cyclopropyl-6-fluoro-1,4-dihydro-4-oxo-7-piperazinyl-quinoline-3-carboxylic acids represented by the following formula (10)

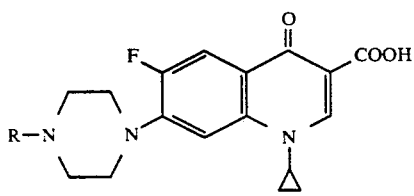

wherein R is H, $CH_3$, $C_2H_5$ or $HOCH_2CH_2$—, and their pharmaceutically acceptable acid addition salts or hydrates.

European Laid-Open Patent Publication No. 113093 and its corresponding Japanese Laid-Open Patent Publication No. 130880/1984 disclose compounds represented by the following formula (11)

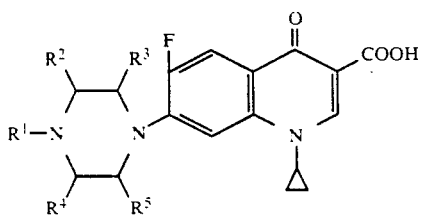

wherein $R^1$ is H or an optionally OH-substituted alkyl group having 1 to 12 carbon atoms, and $R^2$, $R^3$, $R^4$ and $R^5$ are the same or different and each represents an alkyl group having 1 to 4 carbon atoms, provided that at least one of $R^2$ to $R^5$ is the alkyl group, their pharmaceutically acceptable acid addition salts, alkali metal or alkaline earth metal salts or hydrates. The compounds of formulae (10) and (11) do not have a substituent at the 5-position of the quinoline ring as is seen from these formulae.

Japanese Laid-Open Patent Publication No. 174367/1983 (the abstract of which is given in Derwent's World Patent Index, Accession No. 83-823272) discloses compounds represented by the following general formula (12)

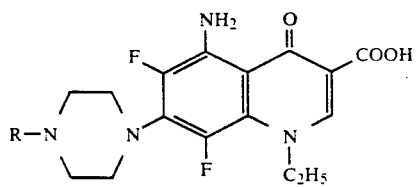

wherein R is H or a lower alkyl group.

European Laid-Open Patent Publication No. 172,651 and its corresponding Japanese Laid-Open Patent Publication No. 43186/1986 disclose compounds represented by the following general formula (13)

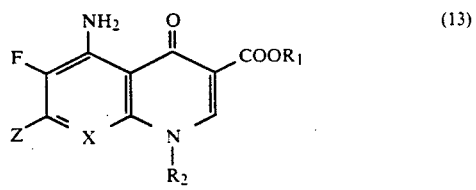

wherein Z represents a specific pyrrolidinyl group or a spiro-amino group, X is CH, CF or N, $R_1$ is H, $C_{1-6}$alkyl, or a cation, and $R_2$ is $C_{1-4}$ alkyl, vinyl, haloalkyl or $C_{2-4}$ hydroxyalkyl or $C_{3-6}$ cycloalkyl. These patent documents, however, do not describe compounds of formula (13) in which Z is a piperazinyl group.

European Laid-Open Patent Specification No. 202763 and its corresponding Japanese Patent Publication No. 243077/1987 disclose compounds represented by the following formula (14)

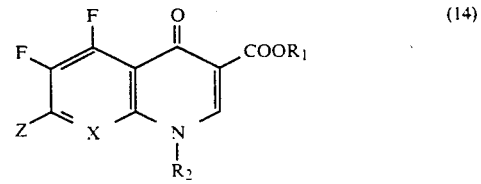

wherein Z is a specific pyrrolidinyl group or a spiro-amino group, X is CF or N, and $R_1$ and $R_2$ are as defined in formula (13).

These patent documents neither describe nor suggest compounds of formula (14) in which Z is a piperazinyl group.

European Laid-Open Patent Publication No. 221463 and its corresponding Japanese Laid-Open Patent Publication No. 277362/1987 disclose compounds represented by the following formula (15)

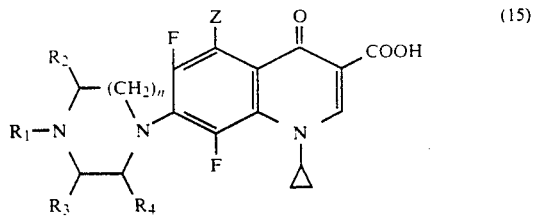

wherein Z is an amino group or a halogen atom, $R_1$ is H, $CH_3$ or $C_2H_5$, $R_2$ is H, $CH_3$ or $CH_2F$, $R_3$ and $R_4$ are the same or different and each represents H or $CH_3$, and n is 1 or 2,
and their pharmaceutically acceptable esters or salts.

European Laid-Open Patent Specification No. 226961 and its corresponding Japanese Laid-Open Patent Publication No. 187459/1987 disclose compounds represented by the following formula (16)

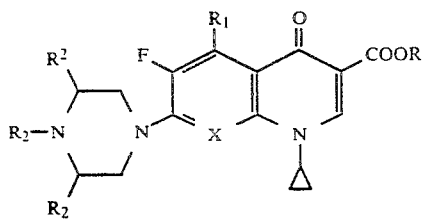

(16)

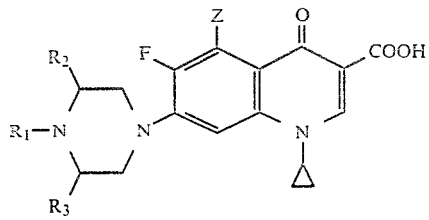

(I)

wherein R is H, a cation or $C_{1-6}$ alkyl, $R_1$ is amino, HO or $C_{1-3}$ alkoxy, X is CH, CBr, CCl, CF, CCF$_3$ or N, and the three $R_2$'s independently represent H or $C_{1-6}$ alkyl.

However, Examples of these patent documents only disclose two compounds in which $R_1$ is amino and X is CF, one compound in which $R_1$ is amino and X is CCl, and one compound in which $R_1$ is OH and X is CF. Production, properties, and antibacterial activities of other compounds that fall within the above formula are not disclosed in these patent documents by specific data.

U. S. Pat. No. 4,668,680 (which resulted from U.S. patent application Ser. No. 808122, one of the two priority applications in the above-cited European Laid-Open Patent Specification No. 226961 and Japanese Laid-Open Patent Publication No. 187459/1987) claims only two compounds of formula (16) in which $R_1$ is amino and X is CF on the basis of the disclosure of its specific working examples.

It is an oject of this invention to provide novel quinoline derivatives of formula (I) and their pharmaceutically acceptable esters and salts.

Another object of this invention is to provide novel quinoline derivatives (I) and their pharmaceutially acceptable esters and salts which have excellent anti-bacterial activity in vitro and in vivo against both Gram-positvie and Gram-negative bacteria.

Still another object of this invention is to provide compounds which have a broad antibacterial spectrum and show excellent activity against the genera Mycoplasma and Chlamydia as well.

Yet another object of this invention is to provide novel compounds (I) and their pharmaceutically acceptable esters and salts, which have excellent properties as pharmaceuticals, such as considerably high solubility in water, good light stability in aqueous solution and good urinary excretion.

A further object of this invention is to provide a process for producing the novel compounds.

A still further object of this invention is to provide a pharmaceutical composition comprising an effective amount of a compound of formula (I) or its pharmaceutically acceptable ester or salt.

A yet further object of this invention is to provide a method of treating a bacterial infection of a warm-blooded animal, which comprises administering the compound or the pharmaceutical composition of the invention to the animal.

Additional objects of the invention along with its advantages will become apparent from the following description.

According to this invention, these objects and advantages of the invention are firstly achieved by a quinoline derivative represented by the following formula wherein Z is an amino group or a halogen atom, and $R_1$, $R_2$ and $R_3$ are the same or different and each represents a hydrogen atom or a lower alkyl group having 1 to 5 carbon atoms, or an ester thereof or a salt of the derivative or the ester.

In the above formula (I), Z is an amino group or a halogen atom. Examples of the halogen atom are fluorine and chlorine, and fluorine is especially preferred.

$R_1$, $R_2$ and $R_3$ are the same or different and each represents a hydrogen atom or an alkyl group having 1 to 5 carbon atoms. The alkyl group may be linear or branched, and may be, for example, methyl, ethyl, propyl, isopropyl, butyl, sec-butyl, iso-butyl, t-butyl or pentyl.

The compound of formula (I), its ester, and salts of these are generically referred to as the compound of this invention.

The compounds of the invention may also exist as hydrates. Hence, these hydrates are also included within the compounds of this invention.

The compounds of the invention include those which have asymmetric carbon atoms for example, when $R_2$ is an alkyl group having 1 to 5 carbon atoms in formula (I), the carbon atom to which the alkyl group is bonded], and therefore exist in optically active forms. Hence, they include D isomers, L isomers and mixtures thereof.

Some of the compounds of this invention have a plurality of asymmetric carbon atoms (for example, when both $R_2$ and $R_3$ are alkyl groups having 1 to 5 carbon atoms, the two carbon atoms to which $R_2$ and $R_3$ are bonded), and therefore can exist as stereoisomers having different configurations. These stereoisomers and their mixtures are also included within the compounds of this invention.

The esters of the compounds of formula (I) include, for example, aliphatic esters, particularly lower alkyl esters having 1 to 5 carbon atoms, such as methyl and ethyl esters; and esters whose alcohol moieties can be easily split off in vivo and converted to the compounds (I), for example acetoxymethyl - esters, pivaloyloxymethyl esters, ethoxycarbonyloxyethyl esters, choline esters, aminoethyl esters (such as dimethylaminoethyl esters or piperidinoethyl esters), 5-indanyl esters, phthalidyl esters, and hydroxyalkyl esters (such as 2-hydroxyethyl esters and 2,3-dihydroxypropyl esters).

The salt of the compound of formula (I) or the salt of its ester should be understood as a salt formed between the compound of formula (I) or its ester with a pharmaceutically acceptable acid or base. Examples of the salts include salts of the compounds of formula (I) or their esters with inorganic acids such as hydrochloric acid and phosphoric acid; with organic acids such as acetic acid, lactic acid, oxalic acid, succinic acid, methanesulfonic acid, maleic acid, malonic acid and gluconic acid; with acidic amino acids such as aspartic acid and glutamic acid; with metals such as sodium, potassium, calcium, magnesium, zinc and silver; with organic bases such as dimethylamine, triethylamine, dicyclohexylamine and benzylamine; and with basic amino acids such as lysine and arginine.

Examples of the compounds of the invention include the following compounds.

5-Amino-1-cyclopropyl-6-fluoro-7-(1-piperazinyl)-1,4-dihydro-4-oxoquinoline-3-carboxylic acid of the formula:

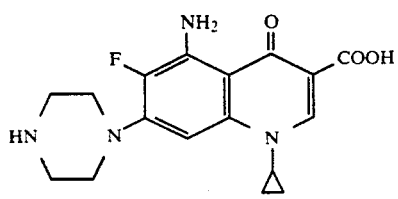

5-Amino-1-cyclopropyl-6-fluoro-7-(4-methyl-1-piperazinyl)-1,4-dihydro-4-oxoquinoline-3-carboxylic acid of the formula:

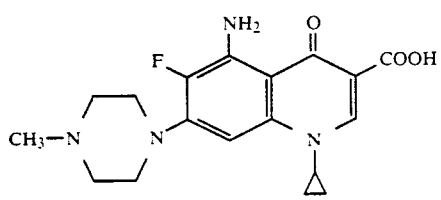

5-Amino-1-cyclopropyl-6-fluoro-7-(3-methyl-1-piperazinyl)-1,4-dihydro-4-oxoquinoline-3-carboxylic acid of the formula:

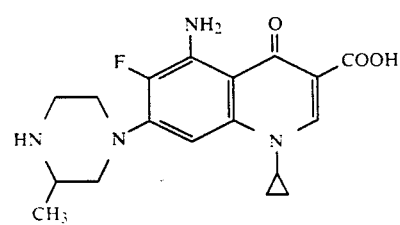

5-amino-1-cyclopropyl-6-fluoro-7-(3,5-dimethyl-1-piperazinyl)-1,4-dihydro-4-oxoquinoline-3-carboxylic acid of the formula:

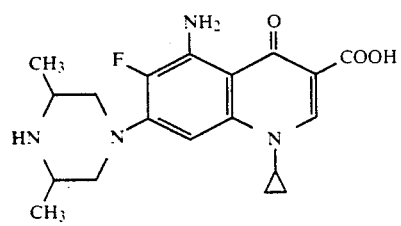

1-Cyclopropyl-5,6-difluoro-7-(1-piperazinyl)-1,4-dihydro-4-oxoquinoline-3-carboxylic acid of the formula:

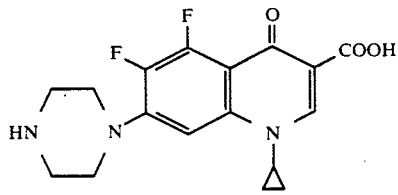

1-Cyclopropyl-5,6-difluoro-7-(4-methyl-1-piperazinyl)-1,4-dihydro-4-oxoquinoline-3-carboxylic acid of the formula:

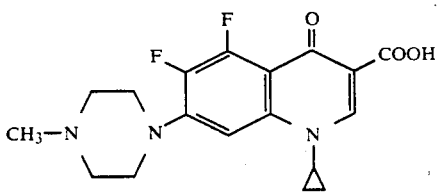

1-Cyclopropyl-5,6-difluoro-7-(3-methyl-1-piperazinyl)-1,4-dihydro-4-oxoquinoline-3-carboxylic acid of the formula:

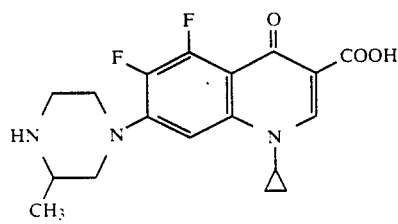

1-Cyclopropyl-5,6-difluoro-7-(3,5-dimethyl-1-piperazinyl)-1,4-dihydro-4-oxoquinoline-3-carboxylic acid of the formula:

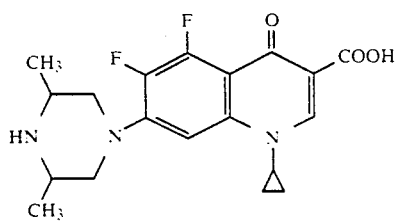

The compounds of this invention show excellent antibacterial activity and a broad antibacterial spectrum in in vitro tests. They are highly active against not only Gram-negative bacteria containing *Pseudomonas aeruginosa* and the genus Seratia, but also Gram-positive bacteria containing Streptococci and Methicillin-resistant *Staphylococcus aureus*, on which conventional quinolone-type antibacterial agents have relatively low activity. In addition, they are highly active against glucose-nonfermenters, anaerobes, and the genera Mycoplasma, Chlamydia and Mycobacterium, against which there are few effective drugs.

The compounds of this invention show an excellent protective effect in vivo on topical or systemic infections caused by various bacteria, and low toxicity in general toxicity tests on animals.

Furthermore, these compounds show good solubility in water, good photo-stability in aqueous solution which are important properties for injectable forms, and good urinary excretion.

Therefore the compounds of this invention are useful as antibacterial agents administrable orally or by injection.

The processes for preparing the compounds of this invention will be described below.

A. Substitution reaction by piperazine derivatives

The compounds of this invention can be produced by reacting a compound represented by the following general formula

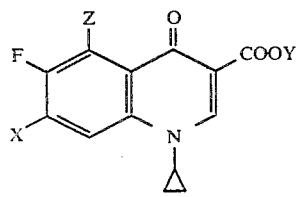

(II)

wherein Z is an amino group or a halogen atom, X is a halogen atom, and Y is a hydrogen atom, a lower alkyl group having 1 to 5 carbon atoms, a diacyloxyboryl group or a difluoroboryl group,
with a piperazine derivative represented by the following general formula

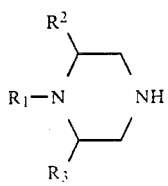

(III)

wherein $R_1$, $R_2$ and $R_3$ are as defined above.

This reaction can be carried out by stirring the starting compounds (II) and (III) at 10° to 180° C. for 10 minutes to 24 hours in an inert solvent. Examples of the inert solvent include alcohols such as ethanol, ethers such as dioxane, tetrahydrofuran and 1,2-dimethoxyethane, aromatic hydrocarbons such as benzene, toluene and xylene, acetonitrile, dimethylformamide, dimethyl sulfoxide, pyridine and water.

Preferably, the above reaction is carried out in the presence of an acid acceptor using the starting compound of formula (III) in an equivalent or slightly excessive amount with regard to the starting compound (II). If desired, the starting compound (III) may be used in excess to make it serve concurrently as the acid acceptor. Examples of the acid acceptor are sodium hydrogen carbonate, sodium carbonate, potassium carbonate, triethylamine, diisopropylethylamine, 1,8-diazabicyclo [5.4.0]undecene-7 (DBU), and pyridine.

The starting compound (II) used in this reaction may, if desired, be used in the form of a boronchelate derivative (compound in which Y is diacyloxyboryl or difluoroboryl group), and after the reaction, the product (chelate compound) is decomposed to give the compound of the invention.

The decomposition reaction can be carried out by treating the chelate compound with an acid or a base in a solvent. Examples of the acid are hydrochloric acid, sulfuric acid and p-toluenesulfonic acid. Examples of the base are sodium hydroxide, potassium hydroxide and triethylamine. Solvents are not specifically limited but preferably water or water-containing solvents are preferred. The reaction temperature is 10° to 150° C.

The starting compounds (II) and/or (III) used in this reaction may, if possible, be used in a form protected by a protective group described in the reaction C hereinafter, and after the reaction, its protective group is removed in a customary manner.

The starting compound (II) can be prepared by the methods described in Referential Examples 1 to 3 or methods substantially in accordance with them.

B. Amination reaction

The compounds of this invention can be prepared by reacting a carboxylic acid represented by the following general formula

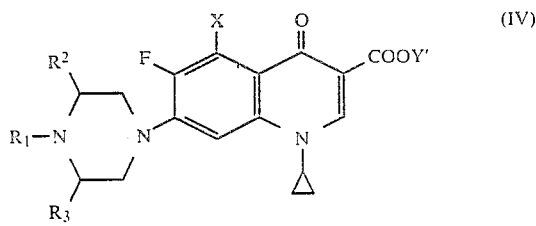

(IV)

wherein X is a halogen atom, Y' is a hyrogen atom or a lower alkyl group having 1 to 5 carbon atoms, and $R_1$, $R_2$ and $R_3$ are as defined above, with ammonia.

This reaction can be carried out by contacting the starting compound (IV) with ammonia for 1 to 50 hours at a temperature of 50° to 150° C. in an inert solvent, for example an alcohol such as ethanol, pyridine, dimethylformamide or water, preferably in a sealed tube.

This reaction is carried out in the presence of an acid acceptor using ammonia in an amount equivalent to, or slightly in excess of, the starting compound (IV). Conveniently, ammonia is used in excess to make it serve also as the acid acceptor. Instead of ammonia, a salt such as ammonium acetate may be caused to act.

The starting compound (IV) used in this reaction may, if possible, be used in a form protected with such a protective group as described below in regard to reaction C, and after the reaction, the protective group is eliminated in a customary manner.

The starting compound (IV) is novel and can be prepared by the reaction A above.

C. Removal of amino protective group

The compound of this invention can be prepared by removing the protective group solvolyzing (also hydrolyzing) or reducing a compound represented by the following general formula

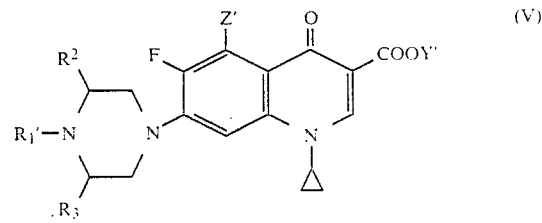

(V)

wherein Z' is an amino group, a halogen atom or a protected amino group, $R'_1$ is a hydrogen atom, a lower alkyl group having 1 to 5 carbon atoms or an amino-protective group, with the proviso that there is at least one amino-protective group in Z' and R'/₁, and R₂, R₃ and Y' are as defined above.

The protective group may be any protective group which can be removed without destroying the structure of the compounds of this invention formed by the reaction. Groups which are normally used as protective groups for the amino group in the field of chemistry of peptides, aminosugars, nucleic acids or beta-lactam compounds may be used in this invention.

The amino protective groups may be split off by solvolysis (including hydrolysis) or reduction depending upon the properties of the protective groups.

Specific examples of the protective groups capable of being eliminated by solvolysis include acyl groups such as formyl, acetyl and trifluoroacetyl; substituted or unsubstituted alkoxycarbonyl groups such as ethoxycarbonyl, t-butoxycarbonyl, benzyloxycarbonyl, p-methoxybenzyloxycarbonyl and beta-(p-toluenesulfonyl)-ethoxycarbonyl; a trityl group, a trimethylsilyl group, an o-nitrophenylsulfenyl group; a diphenylphosphinyl group; and a tetrahydropyranyl group.

This reaction is carried out in a solvent at 0° to 150° C. in the presence or absence of a catalyst such as an acid or base.

Examples of the acid are inorganic acids such as hydrochloric acid, hydrobromic acid, sulfuric acid and phosphoric acid; organic acids such as acetic acid, trifluoroacetic acid, formic acid, and toluenesulfonic acid; Lewis acids such as boron tribromide and aluminum chloride. Examples of the base are hydroxides such as sodium hydroxide and barium hydroxide, carbonates such as sodium carbonate and potassium carbonate; alkali metal alkoxides such as sodium methoxide and sodium ethoxide; and sodium acetate. Usually, water is used as the solvent. Depending upon the property of the compound, another solvent such as ethanol, dioxane, ethylene glycol dimethyl ether, benzene or acetic acid, or a mixed solvent of such a solvent with water may be used.

Examples of protective groups that may be eliminated by reduction include arylsulfonyl groups such as p-toluenesulfonyl; a methyl group substituted by phenyl or benzyloxy, such as benzyl, trityl or benzyloxymethyl; arylmethoxycarbonyl groups such as benzyloxycarbonyl and p-methoxybenzyloxycarbonyl; and halogenoethoxycarbonyl groups such as beta,beta,beta-trichloroethoxycarbonyl and beta-iodoethoxycarbonyl groups.

This reaction uses different reaction conditions depending upon the property of the protective group to be eliminated. For example, it is carried out by treating the compound with a hydrogen stream in an inert solvent at 10° to 60° C. in the presence of a catalyst such as platinum, palladium or Raney nickel (catalytic reduction); or treating it with metallic sodium in liquid ammonia usually at −50° to −20° C.; or by treating it with a metal such as zinc in acetic acid or in an alcohol such as methanol. Examples of the solvent in the catalytic reduction may include ethylene glycol dimethyl ether, dioxane, dimethylformamide, ethanol, ethyl acetate and acetic acid.

The starting compound (V) is a novel compound, and can be prepared by the reactions A and B above.

Where the compounds of this invention obtained by the above processes are esters, they can be converted to compounds of formula (I) by hydrolyzing the ester moiety in a customary manner. If required, the compounds of formula (I) may be esterified in a customary manner to form esters of the compounds of formula (I).

Pharmaceutically acceptable salts of the compounds of formula (I) or their esters may be produced by treating the compounds of formula (I) or esters thereof with acids, or by treating the compounds (I) with bases or metal salts. Acids suitable for salt formation include, for example, hydrochloric acid, phosphoric acid, acetic acid, lactic acid oxalic acid, succinic acid, methanesulfonic acid, maleic acid, malonic acid, gluconic acid, aspartic acid and glutamic acid. Bases or metal salts suitable for salt formation include, for example, metal hydroxides such as sodium hydroxide and potassium hydroxide, metal carbonates such as sodium carbonate and potassium carbonate, zinc chloride, zinc sulfate, zinc nitrate and silver nitrate.

The compounds of this invention prepared as stated above are isolated and purified in a customary manner, and depending upon the isolating and purifying conditions, may be obtained in the form of a salt or a free acid. They may be converted into each other to produce the compounds of this invention in the desired forms.

The stereoisomers of the compounds of this invention can be isolated by a conventional method such as fractional crystallization or chromatography. It is possible to produce compounds of this invention having a specific configuration by the reactions described above using the starting compounds (III) having a corresponding configuration.

The optically active isomers of the compounds of this invention can be separated by known methods.

The compounds (I) thus obtained, their esters, and salts of these are all new compounds and valuable as antibacterial agents since they have very high antibacterial activity. The compounds (I) and their salts can be used not only as medicines for man and animals, but as fish medicines, agricultural chemicals and food preservatives. The esters of the compounds (I) are of course valuable as starting materials for synthesizing the compounds (I). When the esters can be easily transformed into the compounds (I) in vivo, they can exhibit an equivalent effect and are also useful as antibacterial agents.

Compounds (I) of this invention in which Z is a halogen atom are useful as they have antibacterial activity. They are also valuable as starting materials for for compounds (I) in which Z is an amino group.

When the compounds of this invention are used as antibacterial agents for man, it is recommended that they be administered in a dose of 5 mg to 5 g per day once or several times daily, although the dose may be varied depending upon the age, body weight and symptom of a patient, the administration route, etc. The compounds may be administered orally or parenterally.

The compounds of this invention may be administered in their as-obtained powder form, but they are usually administered in the form of a pharmaceutical preparation together with pharmaceutically acceptable adjuvants. Specific examples of the pharmaceutical preparations are tablets, solutions, capsules, granules, fine granules, pellets, powders, syrups, injections, and ointments. These pharmaceutical preprations are prepared by methods known per se. Adjuvants for oral administration are those which are commonly used in the field of formulating pharmaceutical preparations and do not react with the compounds of the invention, such as starch, mannitol, crystalline cellulose, CMC Na, water, ethanol, etc. Adjuvants for injections are those commonly used in the field of injection such as water, isotonic sodium chloride solution, glucose solution and transfusion solution.

The above liquid preparations and ointments can also be used for local treatments in oto-rhinolaryngology or ophthalmology.

The following examples illustrate the production of the compounds of this invention more specifically.

REFERENTIAL EXAMPLE 1

1-Cyclopropyl-5,6,7-trifluoro-1,4-dihydro-4-oxoquinoline-3-carboxylic acid:

(1) 38.8 g of 2,3,4,6-tetrafluorobenzoic acid, a known compound, was treated with thionyl chloride to give 36 g of 2,3,4,6-tetrafluorobenzoyl chloride as an oil. b.p. 87°–89° C. (36 mmHg).

(2) The resulting commpound (36 g) was reacted with sodium diethyl malonate in anhydrous toluene to give diethyl 2,3,4,6-tetrafluorobenzoylmalonate as an oil. Water and a catalytic amount of p-toluenesulfonic acid were added, and the mixture was heated under reflux for 2.5 hours to give 28.4 g of ethyl 2,3,4,6-tetrafluorobenzoylacetate as an oil. b.p. 103°–104° C. (3 mmHg).

(3) The resulting compound (28.4 g) was treated with ethyl orthoformate and acetic anhydride to convert it into ethyl 3-ethoxy-2-(2′,3′,4′,6′-tetrafluorobenzoyl) acrylate and this compound was then treated with cyclopropylamine to give 32.8 g of ethyl 3-cyclopropylamino-2-(2′,3′,4′,6′-tetrafluorobenzoyl) acrylate. m.p. 107°–108° C.

(4) A mixture of 33 g of the resulting compound, 8.85 g of potassium fluoride and 100 ml of dimethylformamide was stirred at 150° to 160° C. for 2 hours, and then allowed to cool to room temperature. Water (300 ml) was added to the reaction mixture, and the crystals were collected by filtration. Chloroform and water were added to the crystals, and the aqueous layer was made alkaline with a saturated aqueous solution of sodium carbonate. The chloroform layer was separated, and dried over anhydrous sodium sulfate. The solvent was evaporated under reduced pressure, and the residue was separated and purified by column chromatography to give the following compounds.

Ethyl 1-cyclopropyl-5,6,7-trifluoro-1,4-dihydro-4-oxoquinoline-3-carboxylate (2.0 g), m.p. 220°–221° C.

Ethyl 1-cyclopropyl-5,7,8-trifluoro-1,4-dihydro-4-oxoquinoline-3-carboxylate (27 g), m.p. 211°–212° C.

(5) A mixture of 1.54 g of ethyl 1-cyclopropyl-5,6,7-trifluoro-1,4-dihydro-4-oxoquinoline-3-carboxylate, 8 ml of glacial acetic acid, 6 ml of water and 1 ml of conc. sulfuric acid was stirred at 120° C. for 1.5 hours. After cooling, the crystals which precipitated were collected by filtration, and washed successively with water and ethanol to give 1.34 g of 1-cyclopropyl-5,6,7-trifluoro-1,4-dihydro-4-oxoquinoline-3-carboxylic acid as colorless needles. m.p. 295°–297° C. (decomp.)

REFERENTIAL EXAMPLE 2

5-Amino-1-cyclopropyl-6,7-difluoro-1,4-dihydro-4-oxoquinoline-3-carboxylic acid:

(1) A mixture of 2.57 g of ethyl 1-cyclopropyl-5,6,7-trifluoro-1,4-dihydro-4-oxoquinoline-3-carboxylate, 1.8 ml of benzylamine and 180 ml of trichloroethylene was heated under reflux for 3 hours and 40 minutes. Water and 10 % hydrochloric acid were added to the reaction mixture to render the aqueous layer acidic. The trichloroethylene layer was separated and dried over anhydrous sodium sulfate. The solvent was evaporated under reduced pressure, and the residue was separated and purified by silica gel column chromatography to give 2.78 g of ethyl 5-benzylamino-1-cyclopropyl-6,7-difluoro-1,4-dihydro-4-oxoquinoline-3-carboxlate. m.p 144°–145° C.

(2) The resulting compound (2.78 g) was dissolved in 100 ml of glacial acetic acid, and catalytically reduced at 60° C. using 0.2 g of 5% palladium-carbon as a catalyst. After a theoretical amount of hydrogen was absorbed, the catalyst was removed by filtration, and the solvent was evaporated under reduced pressure. The residue was recrystallized from acetonitrile to give 2.1 g of ethyl 5-amino-1-cyclopropyl-6,7-difluoro-1,4-dihydro-4-oxoquinoline-3-carboxylate as colorless needles. m.p. 240°–241° C.

(3) A mixture of 2.09 g of the resulting compound, 8 ml of glacial acetic acid, 6 ml of water and 1 ml of conc. sulfuric acid was stirred at 110° C. for 1.5 hours. Water (30 ml) was added to the reaction mixture, and the crystals which precipitated were collected by filtration and successively washed with water and ethanol to give 1.71 g of 5-amino-1-cyclopropyl-6,7-difluoro-1,4-dihydro-4-oxoquinoline-3-carboxylic acid as pale yellow needles. m.p. more than 300° C.

REFERENTIAL EXAMPLE 3

5-Amino-1-cyclopropyl-6,7-difluoro-1,4-dihydro-4-oxoquinoline-3-carboxylic acid:

(3) A mixture of 19.4 g of 2,3,4,6-tetrafluorobenzoic acid, 200 ml of dioxane and 35.3 ml of benzylamine was heated under reflux for 3 hours. The reaction mixture was concentrated to dryness under reduced pressure. Water was added to the residue, and hydrochloric acid was added to adjust the pH of the solution to 3. The solution was then extracted with ethyl acetate. The extract was dried, treated with activated carbon and concentrated. Ether and n-hexane were added to the residue, and the crystals were collected by filtration to give 20.2 g of 2-benzylamino-3,4,6-trifluorobenzoic acid. m.p. 140°–141° C.

(2) A mixture of 21.7 g of the resulting compound, 16.8 ml of acetic anhydride and 200 ml of chloroform was heated under reflux for 9 hours. The reaction mixture was extracted with an aqueous solution of sodium hydroxide having a pH of 9 to 10. The extract was adjusted to pH 3–4 with hydrochloric acid and then extracted with ethyl acetate. The extract was dried and concentrated under reduced pressure. To the residue was added isopropyl ether, and the crystals which precipitated were collected by filtration. There was obtained 17.6 g of 2(N-acetylbenzylamino)-3,4,6-trifluorobenzoic acid. m.p. 150°–153° C.

(3) A mixture of 1.6 g of the resulting compound, 0.99 ml of triethylamine and 10 ml of toluene was cooled with ice, and 3 ml of a toluene solution of 0.62 ml of ethyl chlorocarbonate was added dropwise over the course of 10 minutes. The mixture was stirred for 1 hour, and the precipitate was removed by filtration (reaction mixture A). 780 mg of 92% sodium ethoxide was added to a toluene solution of 1.67 ml of diethyl malonate, and the mixture was stirred at room temperature for 1 hour. Ethanol formed was evaporated, and the reaction mixture A was added dropwise at room temperature to the residue, and the mixture was stirred for 2 hours. The reaction mixture was extracted with an aqueous solution of sodium hydroxide having a pH of 10 to 11. The extract was acidified with hydrochloric acid to a pH of 3 to 4, and then extracted with ethyl acetate. The extract was dried and concentrated to dryness under reduced pressure. The residue was purified by silica gel chromatography (eluent: chloroform) to give 2.3 g of diethyl 3-(N-acetylbenzylamino)-3,4,6-trifluorobenzoylmalonate. Water (10 ml) and 480 mg of p-toluenesulfonic acid monohydrate were added, and the mixture was heated under reflux for 1 hour. After cooling, the mixture was extracted with ethyl acetate. The extract was dried and then concentrated under reduced pressure to give 1.9 g of ethyl 2-(N-acetylbenzylamino)-3,4,6-trifluorobenzoylacetate.

(4) A mixture of 1 g of the resulting compound, 0.6 g of acetic anhydride and 0.64 ml of ethyl orthoformate was heated under reflux for 1.5 hours. The reaction mixture was concentrated to dryness under reduced pressure. The residue was dissolved in isopropyl ether, and under ice cooling, 0.2 ml of cyclopropylamine was added. The mixture was stirred for 1 hour. Ten milliliters of n-hexane was added to the reaction mixture. The crystals which precipitated were collected by filtration to give 993 mg of ethyl 2-(N-acetyl-2'-benzylamino-3',4',6'-trifluorobenzoyl)-3-cyclopropylaminoacrylate. m.p. 119°–121° C.

(5) The resulting compound (26.3 g) was dissolved in 150 ml of tetrahydrofuran, and under ice cooling, 7.1 g of potassium t-butoxide was added little by little, and the mixture was stirred for 30 minutes. It was further stirred at room temperature for 1.5 hours. Ice water was added, and the mixture was adjusted to pH 4–5 with hydrochloric acid, and extracted with chloroform. The extract was dried, and then concentrated to dryness under reduced pressure. Ether was added to the residue, and the crystals were collected by filtration to give 21.4 g of ethyl 5-(N-acetylbenzylamino)-1-cyclopropyl-6,7-difluoro-1,4-dihydro-4-oxoquinoline-3-carboxylate. m.p. 147°–150° C.

(6) The resulting compound (1.0 g) was dissolved in ethanol, and catalytically reduced at 50° to 55° C. using palladium-carbon as a catalyst. The catalyst was removed by filtration, and the filtrate was concentrated to dryness under reduced pressure. To the residue was added 10 ml of a mixed solution of conc. sulfuric acid/glacial acetic acid/water (1:8:6), and the mixture was heated under reflux for 2 hours. Water was added to the reaction mixture, and the crystals which precipitated were collected by filtration and washed with ethanol to give 0.3 g of 5-amino-1-cyclopropyl-6,7-difluoro-1,4-dihydro-4-oxoquinoline-3-carboxylic acid. m.p. more than 300° C.

REFERENTIAL EXAMPLE 4

5-Benzylamino-1-cyclopropyl-6,7-difluoro-1,4-dihydro-4-oxoquinoline-3-carboxylic acid:

Twenty milliliters of a mixture of conc. sulfuric acid, glacial acetic acid and water (1:8:6) was added to 4.4 g of ethyl 5-(N-acetylbenzylamino)-1-cyclopropyl-6,7-difluoro-1,4-dihydro-4-oxoquinoline-3-carboxylate, and the mixture was heated under reflux for 6 hours. After cooling, water was added to the reaction mixture, and the crystals were collected by filtration and successively washed with water and ethanol. The crystals were recrystallized from chloroform/ethanol to give 3.0 g of 5-benzylamino-1-cyclopropyl-6,7-difluoro-1,4-dihydro-4-oxoquinoline-3-carboxylic acid. m.p. 214°–216° C.

EXAMPLE 1

5-Amino-1-cyclopropyl-6-fluoro-7-(1-piperazinyl)-1,4-dihydro-4-oxoquinoline-3-carboxylic acid:

A mixture of 0.42 g of 5-amino-1-cyclopropyl-6,7-difluoro-1,4-dihydro-4-oxoquinoline-3-carboxylic acid, 0.39 g of anhydrous piperazine and 10 ml of pyridine was heated under reflux for 2.5 hours. The reaction mixture was concentrated to dryness under reduced pressure, and the residue was washed with ethanol and then dissolved in water and a 1N aqueous solution of sodium hydroxide. The solution was neutralized with a 10% aqueous solution of acetic acid. The crystals which precipitated were collected by filtration, washed with water, and dried to give 0.44 g of 5-amino-1-cyclopropyl-6-fluoro-7-(1-piperazinyl)-1,4-dihydro-4-oxoquinoline-3-carboxylic acid as pale yellow needles. m.p. 214°–216° C.

EXAMPLE 2

5-Amino-1-cyclopropyl-6-fluoro-7-(4-methyl-1-piperazinyl)-1,4-dihydro-4-oxoquinoline-3-carboxylic acid:

5-Amino-1-cyclopropyl-6,7-difluoro-1,4-dihydro-4-oxoquinoline-3-carboxylic acid and 1-methylpiperazine were reacted and worked up in the same way as in Example 1 to give 5-amino-1-cyclopropyl-6-fluoro-7-(4-methyl-1-piperazinyl)-1,4-dihydro-4-oxoquinoline-3-carboxylic acid. m.p. 216°–218° C.

EXAMPLE 3

5-Amino-1-cyclopropyl-6-fluoro-7-(3-methyl-1-piperazinyl)1,4-dihydro-4-oxoquinoline-3-carboxylic acid:

A mixture of 1.0 g of 5-amino-1-cyclopropyl-6,7-difluoro-1,4-dihydro-4-oxoquinoline-3-carboxylic acid, 1.18 g of 2-methylpiperazine and 10 ml of pyridine was heated under reflux for 3 hours. The reaction mixture was concentrated under reduced pressure, and the residue was dissolved in 28% aqueous ammonia. The solution was neutralized with a 10% aqueous solution of acetic acid and cooled with ice. The crystals were collected by filtration, dissolved in a 10% aqueous solution of acetic acid, treated with activated charcoal, adjusted to pH 8–9 with 29% aqueous ammonia, and cooled with ice. The crystals were collected by filtration and washed successively with water and ethanol to give 0.80 g of 5-amino-1-cyclopropyl-6-fluoro-7-(3-methyl-1-piperazinyl)-1,4-dihydro-4-oxoquinoline-3-carboxylic acid. m.p. 181°–183° C.

EXAMPLE 4

5-Amino-1-cyclopropyl-6-fluoro-7-(cis-3,5-dimethyl-1-piperazinyl)-1,4-dihydro-4-oxoquinoline-3-carboxylic acid and its hydrochloride:

(1) A mixture of 280 mg of 5-amino-1-cyclopropyl-6,7-difluoro-1,4-dihydro-4-oxoquinoline-3-carboxylic acid, 542 mg of cis-2,6-dimethylpiperazine and 10 ml of pyridine was heated under reflux for 2.5 hours. The solvent was evaporated under reduced pressure. To the residue was added a 1N aqueous solution of sodium hydroxide, and the insoluble matter was removed by filtration. A 10% aqueous solution of acetic acid was added to the filtrate to adjust its pH to 8. The solution was then extracted with chloroform. The chloroform layer was dried with sodium sulfate, and concentrated under reduced pressure. Acetonitrile was added to the residue, and the mixture was cooled with ice. The crystals were collected by filtration, and recrystallized from aqueous ammonia to give 250 mg of 5-amino-1-cyclopropyl-6-fluoro-7-(cis-3,5-dimethyl-1-piperazinyl)-1,4-dihydro-4-oxoquinoline-3-carboxylic acid. m.p. 253°–254° C.

(2) The resulting compound was dissolved in a 1N aqueous solution of sodium hydroxide, and 10% hydrochloric acid was added to the solution to acidify it. The crystals which precipitated were collected by filtration and washed successively with water and ethanol to give 5-amino-1-cyclopropyl-6-fluoro-7-(cis-3,5-dimethyl-1-piperazinyl)-1,4-dihydro-4-oxoquinoline-3-carboxylic acid hydrochloride. m.p. more than 300° C.

EXAMPLE 5

5-Amino-1-cyclopropyl-6-fluoro-7-(cis-3,5-dimethyl-1-piperazinyl)-1,4-dihydro-4-oxoquinoline-3-carboxylic acid:

(1) Ethyl 5-amino-1-cyclopropyl-6,7-difluoro-1,4-dihydro-4-oxoquinoline-3-carboxylate and cis-3,5-dimethylpiperazine were reacted in the same way as in Example 4 to give ethyl 5-amino-1-cyclopropyl-6-fluoro-7-(cis-3,5-dimethyl-1-piperazinyl)-1,4-dihydro-4-oxoquinoline-3-carboxylate. It was recrystallized from ethyl acetate. m.p. 194°–196° C.

(2) A mixture of conc. sulfuric acid, glacial acetic acid and water (1:8:6) was added to the resulting compound, and the mixture was heated under reflux. The reaction mixture was worked up as in Example 4 to give 5-amino-1-cyclopropyl-6-fluoro-7-(cis-3,5-dimethyl-1-piperazinyl)-1,4-dihydro-4-oxoquinoline-3-carboxylic acid. m.p. 253°–254° C.

EXAMPLE 6

5-Amino-1-cyclopropyl-6-fluoro-7-(3-methyl-1-piperazinyl)-1,4-dihydro-4-oxoquinoline-3-carboxylic acid:

(1) A mixture of 5-amino-1-cyclopropyl-6,7-difluoro-1,4-dihydro-4-oxoquinoline-3-carboxylic acid, 1-acetyl-2-methylpiperazine and pyridine was heated under reflux for 5 hours. The reaction mixture was concentrated under reduced pressure, and the residue was dissolved in aqueous ammonia. The solution was neutralized with an aqueous solution of acetic acid and cooled with ice. The crystals were collected by filtration to give 7-(4-acetyl-3-methyl-1-piperazinyl)-5-amino-1-cyclopropyl-6-fluoro-1,4-dihydro-4-oxoquinoline-3-carboxylic acid. It was recrystallized from ethanol/chloroform. m.p. 269°–271° C.

(2) A mixture of the resulting compound, a 10% aqueous solution of sodium hydroxide and ethanol was heated under reflux for 12 hours. The reaction mixture was neutralized with an aqueous solution of acetic acid. The crystals which precipitated were collected by filtration to give 5-amino-1-cyclopropyl-6-fluoro-7-(3-methyl-1-piperazinyl)-1,4-dihydro-4-oxoquinoline-3-carboxylic acid. m.p. 181°–183° C.

EXAMPLE 7

5-Amino-1-cyclopropyl-6-fluoro-7-(3-methyl-1-piperazinyl)-1,4-dihydro-4-oxoquinoline-3-carboxylic acid:

(1) A mixture of 3.0 g of 5-benzylamino-1-cyclopropyl-6,7-difluoro-1,4-dihydro-4-oxoquinoline-3-carboxylic acid, 2.5 g of 2-methylpiperazine and 30 ml of pyridine was heated under reflux for 5 hours. The reaction mixture was concentrated under reduced pressure. Water was added to the residue, and the solution was acidified with acetic acid and treated with activated charcoal. It was then neutralized with aqueous ammonia. The crystals which precipitated were collected by filtration to give 2.9 g of 5-benzylamino-1-cyclopropyl-6-fluoro-7-(3-methyl-1-piperazinyl)-1,4-dihydro-4-oxoquinoline-3-carboxylic acid. m.p. 129°–130° C.

(2) The resulting compound was dissolved in a mixture of acetic acid and ethanol, and catalytically reduced by using 5% palladium-carbon as a catalyst. The catalyst was removed by filtration, and the filtrate was concentrated under reduced pressure. Water was added to the residue, and the pH of the solution was adjusted to 8 with aqueous ammonia. The crystals which precipitated were collected by filtration to give 5-amino-1-cyclopropyl-6-fluoro-7-(3-methyl-1-piperazinyl)-1,4-dihydro-4-oxoquinoline-3-carboxylic acid. m.p. 181°–183° C.

EXAMPLE 8

5-Amino-1-cyclopropyl-6-fluoro-7-(3-methyl-1-piperazinyl)-1,4-dihydro-4-oxoquinoline-3-carboxylic acid:

(1) A mixture of 5-benzylamino-1-cyclopropyl-6,7-difluoro-1,4-dihydro-4-oxoquinoline-3-carboxylic acid, 1-acetyl-2-methylpiperazine and pyridine was heated under reflux. The reaction mixture was concentrated under reduced pressure, and water was added to the residue. The mixture was extracted with chloroform. The extract was dried and chloroform was evaporated. Ethanol was added to the residue, and the crystals were collected by filtration to give 7-(4-acetyl-3-methyl-1-piperazinyl)-5-benzylamino-1-cyclopropyl-6-fluoro-1,4-dihydro-4-oxoquinoline-3-carboxylic acid. It was recrystallized from ethanol/diisopropyl ether. m.p. 235°–236° C.

(2) The resulting compound was catalytically reduced as in Example 7, (2) and then hydrolyzed as in Example 6, (2) to give 5-amino-1-cyclopropyl-6-fluoro-7-(3-methyl-1-piperazinyl)-1,4-dihydro-4-oxoquinoline-3-carboxylic acid. m.p. 181°–183° C.

EXAMPLE 9

1-Cyclopropyl-5,6-difluoro-7-(4-methyl-1-piperazinyl)-1,4-dihydro-4-oxoquinoline-3-carboxylic acid:

(1) A mixture of 0.41 g of boric acid and 5 ml of acetic anhydride was heated at 80° C. for 1.5 hours, and 1.25 g of 1-cyclopropyl-5,6,7-trifluoro-1,4-dihydro-4-oxoquinoline-3-carboxylic acid was added. The mixture was refluxed for 2 hours and evaporated under reduced pressure. The residue was recrystallized from chloroform/ethyl acetate to give 1.62 g of 1-cyclopropyl-5,6,7-trifluoro-1,4-dihydro-4-oxoquinoline-3-carboxylic acid B(OCOCH$_3$)$_2$ chelate. m.p. more than 300° C.

(2) A mixture of 411 mg of the resulting compound, 0.11 ml of 1-methylpiperazine, 0.17 ml of triethylamine and 4 ml of dimethylformamide was stirred at room temperature for 2 hours, and the reaction mixture was concentrated to dryness under reduced pressure. The residue was dissolved in 2 ml of acetone, and 1.5 ml of conc. hydrochloric acid was added. The mixture was stirred at room temperature for 30 minutes. The reaction mixture was concentrated to dryness under reduced pressure. The residue was dissolved in water, neutralized with a 1N aqueous solution of sodium hydroxide, and then extracted with chloroform. The solvent was evaporated under reduced pressure. The residue was recrystallized from ethyl acetate to give 320 mg of 1-cyclopropyl-5,6-difluoro-7-(4-methyl-1- piperazinyl)-1,4-dihydro-4-oxoquinoline-3-carboxylic acid. m.p. 253°–255° C. (decomp.).

EXAMPLE 10

1-Cyclopropyl-5,6-difluoro-7-(1-piperazinyl)-1,4-dihydro-4-oxoquinoline-3-carboxylic acid:

(1) A mixture of 1-cyclopropyl-5,6,7-trifluoro-1,4-dihydro-4-oxoquinoline-3-carboxylic acid B(O-$COCH_3$)$_2$ chelate, 1-formylpiperazine, triethylamine and ethanol was stirred at room temperature for 1 hour. The reaction mixture was treated as in Example 9, (2) to give 1-cyclopropyl-5,6-difluoro-7-(4-formyl-1-piperazinyl)-1,4-dihydro-4-oxoquinoline-3-carboxylic acid. m.p. 297°–299° C. (decomp.).

(2) A mixture of 120 mg of the resulting compound and 5 ml of 20% hydrochloric acid was stirred at 100 to 120° C. for 1.5 hours. The reaction mixture was concentrated to dryness under reduced pressure. The residue was dissolved in water and treated with activated charcoal. The solution was made alkaline with concentrated aqueous ammonia. The crystals which precipitated were collected by filtration, washed with water and dried to give 80 mg of 1-cyclopropyl-5,6-difluoro-7-(1-piperazinyl)-1,4-dihydro-4-oxoquinoline-3-carboxylic acid. m.p. more than 300° C.

EXAMPLE 11

1-Cyclopropyl-5,6-difluoro-7-(3-methyl-1-piperazinyl)-1,4-dihydro-4-oxoquinoline-3-carboxylic acid:

A mixture of 1-cyclopropyl-5,6,7-trifluoro-1,4-dihydro-4-oxoquinoline-3-carboxylic acid B(OCOCH$_3$)$_2$ chelate, 2-methylpiperazine, triethylamine and dimethyl sulfoxide was stirred at room temperature for 30 minutes. Water was added to the reaction mixture, and the crystals which precipitated were collected by filtration. A 1N aqueous solution of sodium hydroxide was added, and the mixture was stirred at 80° C. for 10 minutes. The reaction mixture was neutralized with acetic acid, and the crystals which precipitated were collected by filtration to give 1-cyclopropyl-5,6-difluoro-7-(3-methyl-1-piperazinyl)-1,4-dihydro-4-oxoquinoline-3-carboxylic acid.

EXAMPLE 12

1-Cyclopropyl-5,6-difluoro-7-(cis-3,5-dimethyl-1-piperazinyl)-1,4-dihydro-4-oxoquinoline-3-carboxylic acid:

0.32 g of 1-cyclopropyl-5,6,7-trifluoro-1,4-dihydro-4-oxoquinoline-3-carboxylic acid B(OCOCH$_3$)$_2$ chelate was dissolved in 6 ml of dimethylformamide. While the solution was stirred under ice cooling, a solution of 89 mg of cis-2,6-dimethylpiperazine and 0.13 ml of triethylamine in 2 ml of dimethylformamide was added to the solution, and the mixture was stirred for 30 minutes. The mixture was then stirred at room temperature for 40 minutes, and 3 ml of conc. hydrochloric acid was added. The mixture was stirred overnight at room temperature. The crystals were collected by filtration, and dissolved in a 10% aqueous solution of acetic acid. The solution was adjusted to pH 8 with a 1N aqueous solution of sodium hydroxide. After cooling with ice, the crystals were collected by filtration. The crystals were dissolved in a 1N aqueous solution of sodium hydroxide. The solution was adjusted to pH 8 with a 10% aqueous solution of acetic acid, and the solution was cooled with ice. The crystals were collected by filtration and washed with water to give 80 mg of 1-cyclopropyl-5,6-difluoro-7-(cis-3,5-dimethyl-1-piperazinyl)-1,4-dihydro-4-oxoquinoline-3-carboxylic acid. m.p 259°–260° C.

EXAMPLE 13

5-Amino-1-cyclopropyl-6-fluoro-7-(1-piperazinyl)-1,4-dihydro-4-oxoquinoline-3-carboxyclic acid:

1-Cyclopropyl-5,6-difluoro-7-(1-piperazinyl)-1,4-dihydro-4-oxoquinoline-3-carboxylic acid and 28% aqueous ammonia were heated at 100° C. for 48 hours in a sealed tube. The reaction mixture was concentrated to dryness under reduced pressure. The residue was dissolved in a 1N aqueous solution of sodium hydroxide, and neutralized with a 10% aqueous solution of acetic acid. The crystals which precipitated were collected by filtration to give 5-amino-1-cyclopropyl-6-fluoro-7-(1-piperazinyl)-1,4-dihydro-4-oxoquinoline-3-carboxylic acid. m.p. 214°–216° C.

EXAMPLE 14

5-Amino-1-cyclopropyl-6-fluoro-7-(4-methyl-1-piperazinyl)-1,4-dihydro-4-oxoquinoline-3-carboxylic acid:

In a sealed tube, 1-cyclopropyl-5,6-difluoro-7-(4-methyl-1-piperazinyl)-1,4-dihydro-4-oxoquinoline-3-carboxylic acid was aminated with ammonia/ethanol as in Example 13 to give 5-amino-1-cyclopropyl-6-fluoro-7-(4-methyl-1-piperazinyl)-1,4-dihydro-4-oxoquinoline-3-carboxlic acid. m.p 216°–218° C.

EXAMPLE 15

5-Amino-1-cyclopropyl-6-fluoro-7-(3-methyl-1-piperazinyl)-1,4-dihydro-4-oxoquinoline-3-carboxylic acid:

In a sealed tube, 1-cyclopropyl-5,6-difluoro-7-(3-methyl-1-piperazinyl)-1,4-dihydro-4-oxoquinoline-3-carboxylic acid was aminated with ammonia/dimethylformamide as in Example 13 to give 5-amino-1-cyclopropyl-6-fluoro-7-(3-methyl-1-piperazinyl)-1,4-dihydro-4-oxoquinoline-3-carboxylic acid. m.p. 181°–183° C.

EXAMPLE 16

5-Amino-1-cyclopropyl-6-fluoro-7-(cis-3,5-dimethyl-1-piperazinyl)-1,4-dihydro-4-oxoquinoline-3-carboxylic acid:

In a sealed tube, 1-cyclopropyl-5,6-difluoro-7-(cis-3,5-dimethyl-1-piperazinyl)-1,4-dihydro-4-oxoquinoline-3-carboxylic acid and 28% aqueous ammonia were heated at 100° C. for 48 hours. The reaction mixture was concentrated under reduced pressure. A 1N aqueous solution of sodium hydroxide was added to the residue, and the insoluble matter was removed by filtration. A 10% aqueous solution of acetic acid was added to the filtrate to adjust its pH to 8, and it was then extracted with chloroform. The extract was dried and concentrated. Acetonitrile was added to the residue, and the mixture was cooled with ice. The crystals were collected by filtration and recrystallized from aqueous ammonia to give 5-amino-1-cyclopropyl-6-fluoro-7-(cis-3,5-dimethyl-1-piperazinyl)-)-1,4-dihydro-4-oxoquinoline-3-carboxylic acid. m.p. 253°–254° C.

EXAMPLE 17

5-Amino-1-cyclopropyl-6-fluoro-7-(3-methyl-1-piperazinyl)-1,4-dihydro-4-oxoquinoline-3-carboxylic acid:

(1) In a sealed tube, 7-(4-acetyl-3-methyl-1-piperazinyl)-1-cyclopropyl-5,6-difluoro-1,4-dihydro-4-oxoquinoline-3-carboxylic acid was aminated as in Example 13 to give 7-(4-acetyl-3-methyl-1-piperazinyl)-5-amino-1-cyclopropyl-6-fluoro-1,4-oxoquinoline-3-carboxylic acid. m.p. 269°–271° C.

(2) The resulting compound was hydrolyzed as in Example 6, (2) to give 5-amino-1-cyclopropyl-6-fluoro-7-(3-methyl-1-piperazinyl)-1,4-dihydro-4-oxoquinoline-3-carboxylic acid. m.p. 181°–183° C.

Examples 18 to 20 illustrate pharmaceutical compositions containing the compounds of the invention as active ingredients.

EXAMPLE 18

| Compound of this invention | 250 g |
|---|---|
| Starch | 50 g |
| Lactose | 35 g |
| Talc | 15 g |

The above components were blended with ethanol and granulated and filled into 1,000 capsules in accordance with conventional methods.

EXAMPLE 19

| Compound of this invention | 250 g |
|---|---|
| Starch | 54 g |
| Calcium carboxymethyl cellulose | 40 g |
| Microcrystalline cellulose | 50 g |
| Magnesium stearate | 6 g |

The above components were blended with ethanol, granulated and made into tablets in a manner known per se. Thus, 1,000 tablets each weighing 400 mg were formed.

EXAMPLE 20

| Compound of this invention | 50 g |
|---|---|
| Lactic acid | 120 g |

The above components were dissolved in distilled water sufficient to make ten liters solution. The solution was adjusted to pH about 4 with an aqueous sodium hydroxide solution, and then filled in ampules (10 ml) to make an injectable solution.

The chemotherapeutic activities and some other properties of the compounds of this invention are shown in Examples 21–26 hereinbelow. The compounds tested comprise:

Compound 1: 5-amino-1-cyclopropyl-6-fluoro-7-1-piperazinyl)-1,4-dihydro-4-oxo-quinoline-3-carboxylic acid, Compound 2: 5-amino-1-cyclopropyl-6-fluoro-7-(cis-3,5-dimethyl-1-piperazinyl)-1,4-dihydro-4-oxoquinoline-3-carboxylic acid, Compound A: 1-cyclopropyl-6-fluoro-7-(1-piperazinyl)-1,4-dihydro-4-oxoquinoline-3-carboxylic acid anhydride (cyprofloxacin), Compound B: 5-amino-1-cyclopropyl-6,8-difluoro-7-(1-piperazinyl)-1,4-dihydro-4-oxoquinoline-3-carboxylic acid.

EXAMPLE 21

The antibacterial activity in vitro is shown in Table 1. The figures in the table show minimum inhibitory concentrations (MIC) ($\mu$g/ml), calculated for free base. The minimum inhibitory concentration was determined by the twofold agar-dilution method, which was recommended by Japan Society of Chemotherapy (Chemotherapy, 29(1), 76(1981)), using Muller-Hinton agar. One loopful of an overnight culture of test organisms in Mueller-Hinton broth was inoculated onto 10-ml drug-containing agar layers in petri dishes. Bacterial inocula contained approximately $10^6$ colonyl-forming units. Bacterial growth was observed after 20-hour incubation at 37° C. The MIC was defined as the lowest drug concentration which prevented visible bacterial growth.

TABLE 1

In vitro antibacterial activity

| Strains | Compounds | | | |
|---|---|---|---|---|
| | 1 | 2 | A | B |
| S. aureus 209 JC-1 | 0.025 | 0.1 | 0.1 | 0.05 |
| S. aureus Terajima | 0.05 | 0.05 | 0.1 | 0.025 |
| S. aureus No. 80 | 0.05 | 0.025 | 0.39 | 0.05 |
| S. epidermidis No. 8 | 0.025 | 0.1 | 0.1 | 0.05 |
| S. pyogenes Cook | 0.2 | 0.39 | 0.2 | 0.2 |
| E. coli NIHJ JC-2 | 0.0063 | 0.025 | 0.0063 | 0.0063 |
| E. coli P-5101 | 0.0063 | 0.025 | 0.0063 | 0.0063 |
| S. marcescens IFO 3736 | 0.1 | 0.78 | 0.05 | 0.1 |
| P. Aeruginosa 12 | 0.05 | 0.39 | 0.1 | 0.1 |
| Flavobacterium sp P-7201 | 0.1 | 0.1 | 0.39 | 0.1 |

EXAMPLE 22

In vivo efficacy against systemic infections in mice is shown in Table 2.

Compounds were each suspended in 0.4% carboxymethyl cellulose. Each of the suspensions was orally administered to mice infected with each of the test organisms under the conditions shown hereinbelow, and the median effective dose ($ED_{50}$) was calculated by probit analysis. The numerals in the table shown $ED_{50}$ (mg/Kg) value, calculated for free base.

Experimental conditions:
Mice: Male mice (Std-ddY) weighing about 20 g
Infection:
Staphylococcus aureus 50774
  Intravenous infection with $5 \times 10^8$ cells per mouse suspended in saline.
Streptococcus pneumoniae 1 Neufeld
  Intraperitoneal infection with $3 \times 10^3$ cells per mouse suspended in brain heart infusion broth.
Streptococcus pyogenes A65
  Intraperitoneal infection with $3 \times 10^7$ cells per mouse suspended in brain heart infusion broth.
Pseudomonas aeruginosa 12
  Intraperitoneal infection with about $5 \times 10^3$ cells per mouse suspended in tryptosoy broth with 4% mucin.
Medication:
  Four times, immediately, 6, 24 and 30 hours after infection for Streptococcus pneumoniae 1. Twice, immediately and 6 hours after infection for other organisms.
Observation:
  For 14 days for Staphylococcus aureus 50774 and Streptocuccus pneumoniae 1 Neufeld. For 7 days for other organisms.

TABLE 2

In vivo efficacy against systemic infections in mice

| Organism | Compound | | |
|---|---|---|---|
| | 2 | A | B |
| S. aureus 50774 | 1.41 | 8.24 | — |
| S. pyogenes A65 | 11.6 | 23.9 | >50 |
| S. pneumoniae I Neufeld | 10.2 | 31.3 | 20.8 |
| P. aeruginosa 12 | 1.98 | 2.78 | — |

EXAMPLE 23

The antimycoplasma activity is shown in Table 3. The figures in the table show minimum inhibitory concentrations (MIC), ($\mu$g/ml), calculated for free base.

Minimum inhibitory concentrations (MIC) were determined by the twofold agar dilution method. The media used were Chanock broth and agar PPLD broth and agar (Difco) supplemented with 20% horse serum and 10% fresh yeast extract). A 2–3 day broth culture of organisms was diluted with Chanock broth to a cell density of about $10^6$ cells/ml. One loopful (about 1 micrometer) of the organism dilution was spotted onto 10-ml drug containing Chanock agar in petri dishes using a multiple inoculator (Cathra International). The petri dishes were incubated at 37° C. for 7 and 2 days for Mycoplasma pneumoniae and other Mycoplasma spp. respectively. Incubation was performed anaerobically using the Gaspak anaerobic system (BBL) for M. buccale, M. fermentans, M. hominis, M. orale and M. salivarium, and aerobically for other Mycoplasma spp. The MIC was defined as the lowest compound concentration at which no growth of organism was detected.

TABLE 3

Antimycoplasma activity

| Organism | Compound | | |
|---|---|---|---|
| | 1 | 2 | A |
| M. pneumoniae Mac | 0.1 | 0.1 | 0.78 |
| A. laidlawii PG-8 | 0.1 | 0.05 | 0.39 |
| M. arginini G-230 | 0.1 | 0.05 | 0.39 |
| M. buccale CH-20249 | 0.1 | 0.05 | 0.39 |
| M. fermentans PG-18 | 0.1 | 0.025 | 0.2 |
| M. hominis PG-21 | 0.39 | 0.1 | 1.56 |
| M. orale CH-19299 | 0.39 | 0.39 | 1.56 |
| M. salivarium PG-20 | 1.56 | 0.39 | 3.13 |
| M. hyorhinis BST-7 | 0.1 | 0.05 | 0.39 |

EXAMPLE 24

The antichlamydia activity is shown in Table 4. The figures in the table show minimum inhibitory concentrations (MIC), ($\mu$g/ml), calculated for free base.

Minimum inhibitory concentrations (MIC) were determined as follows. McCoy cells were freshly cultured in Eagle's minimum essential medium (EMEM) (Flow) supplemented with 4% fetal bovine serum and 0.03% L-glutamine. The cells were trypsinized and suspended in the same culture medium at a cell concentration of $1-2 \times 10^5$ cells/ml. One ml of the cell suspension was pipetted into flat-bottomed plastic tubes (14 mm in diameter) containing a cover slip (12 mm in diameter). The tubes were incubated in 5% $CO_2$-air at 36° C. for 20 hours. One-half ml of a chlamydial suspension (ca. $1-4 \times 10^3$ inclusion body forming units) was added into each tube, which was then centrifuged at $1500 \times g$ for 60 minutes. The tubes were incubated for 1 hour at 36° C. The medium was changed with 1 ml of EMEM supplemented with 8% fetal bovine serum, 0.03% L-blutamine, 1$\mu$g/ml cycloheximide and 0.5% glucose, and containing drugs at various concentrations. After further incubation at 36° C. for 40–48 hours, the cells on the cover glasses were stained with the Giemsa's solution. Inclusion bodies in the cells on the cover glasses were observed with a microscope at a magnification of 200–400. The MIC was defined as the lowest drug concentration where there were no inclusion bodies in all the cells on the cover slip.

TABLE 4

Antichlamydia activity

| Organism | Compound | | |
|---|---|---|---|
| | 1 | 2 | A |
| C. Trachomatics G/ur 931 | 0.25 | 0.063 | 1 |
| C. Trachomatics G/ur 1317 | 0.25 | 0.063 | 2 |
| C. Trachomatics G/ur 1467 | 0.25 | 0.063 | 1 |
| C. Trachomatics G/ur 1483 | 0.25 | 0.063 | 1 |

EXAMPLE 25 (Acute toxicity)

A suspension containing each of compounds of this invention in various concentrations was orally given to male mice (ddY) at a dose of 0.1 ml per 10 g of body weight. The number of dead mice was counted after 7 days, and the value of median lethal dose ($LD_{50}$, mg/kg) was calculated in accordance with the Behrens-Kaerber method. The results are shown in Table 5.

TABLE 5

Acute oral toxicity in mice

| Compound | $LD_{50}$ (mg/kg) |
|---|---|
| 1 | >2000 |
| 2 | >2000 |

EXAMPLE 26

The photo-stability in aqueous solution is shown in Table 6.

Each compound was dissolved in 0.1N hydrochloric acid to give an acidic solution (0.3 mg/ml for compound 2, 0.5 mg/ml for other compounds), or in 0.1N aqueous sodium hydroxide to give an alkaline solution (0.5 mg/ml for all compounds). The solution in a 10 ml colorless flask was exposed at 20° C. to the light of a fluorescent lamp (6000 luxes) for 100 hours. The amounts of the compound in the solution at the beginning and after 100 hours were determined by high performance liquid chromatography. The figures in the table show residual percent (%) after 100 hours.

TABLE 6

Photo-stability in aqueous solution

| Sample | Compound | | |
|---|---|---|---|
| | 1 | 2 | B |
| Acidic solution | 92.7 | 90.3 | 57.0 |
| Alkaline solution | 88.2 | 87.6 | 32.5 |

EXAMPLE 27

A suspension containing each of compounds was orally administered to mice at a dose of 5 mg/kg. Urine was collected over a period of 24 hours after adminstration. The levels of the compounds in urine were determined by the thin-layer cup-plated method using Escherichia coli Kp as an indicator organism.

TABLE 7

| | Urinary excretion in mice | |
|---|---|---|
| Compound | 2 | C |
| Urinary recovery for 24 hours (%) | 8.33 | 4.51 |

Compound C: 5-amino-1-cyclopropyl-6,8-difluoro-7-(3,5-dimethyl-1-piperazinyl)-1,4-dihydro-4-oxoquinoline-3-carboxylic acid

What is claimed is:

1. A quinoline compound of the formula

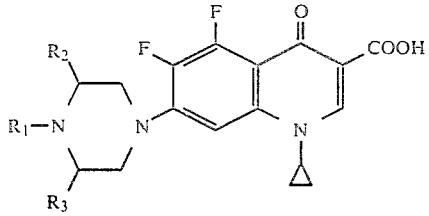

wherein $R_1$ represents a hydrogen atom, and $R_2$ and $R_3$ are the same or different and each represents a hydrogen atom or a methyl group, or an ester thereof or a salt of the compound or ester thereof.

2. A quinoline compound of claim 1 which is 1-cyclopropyl-5,6-difluoro-7-(3,5-dimethyl-1-piperazinyl)-1,4-dihydro-4-oxoquinoline-3-carboxylic acid.

3. A quinoline compound of claim 1 which is 1-cyclopropyl-5,6-difluoro-7-(3-methyl-1-piperazinyl)-1,4-dihydro-4-oxoquinoline-3-carboxylic acid.

4. A quinoline compound of claim 1 which is 1-cyclopropyl-5,6-difluoro-7-(1-piperazinyl)-1,4-dihydro-4-oxoquinoline-3-carboxylic acid.

* * * * *

UNITED STATES PATENT AND TRADEMARK OFFICE
CERTIFICATE OF CORRECTION

PATENT NO. : 5,013,841
DATED : May 7, 1991
INVENTOR(S) : Jun-Ichi Matsumoto, et. al.

It is certified that error appears in the above-identified patent and that said Letters Patent is hereby corrected as shown below:

Column 4, line 33, before "for" insert an opening bracket --[--

Column 19, line 5, change "1,4-oxoquinoline" to read -- -1,4-dihydro-4-oxoquinoline- --.

Column 20, line 40, change "shown" to --show--.

Column 21, line 18, before "PPLD" insert an opening bracked --[--
line 20, change "extract)" to --extract]--.

Signed and Sealed this

Twenty-ninth Day of December, 1992

Attest:

DOUGLAS B. COMER

Attesting Officer          Acting Commissioner of Patents and Trademarks

UNITED STATES PATENT AND TRADEMARK OFFICE
CERTIFICATE OF CORRECTION

PATENT NO. : 5,013,841
DATED : May 7, 1991
INVENTOR(S) : JUN-ICHI MATSUMOTO, AKIRA MINAMIDA, MASAHIRO FUJITA, TOHRU HIROSE, JUNJI NAKANO, SHINICHI NAKAMURA

It is certified that error appears in the above-identified patent and that said Letters Patent is hereby corrected as shown below:

Column 22, line 29, delete "The results are shown in Table 5.";

lines 30 to 60, delete in their entirety;

line 62, change "EXAMPLE 27" to read --EXAMPLE 26--.

Column 23, line 1, change "Table 7" to read --Table 5--.

Signed and Sealed this

Twenty-second Day of February, 1994

Attest:

BRUCE LEHMAN

Attesting Officer

Commissioner of Patents and Trademarks